(12) United States Patent
Pade

(10) Patent No.: US 6,948,981 B2
(45) Date of Patent: Sep. 27, 2005

(54) COMPACT COUPLER PLUG, PARTICULARLY FOR A PLANAR BROADBAND LAMBDA PROBE, IN WHICH SINGLE-CONDUCTOR SEALS ARE PREVENTED FROM BEING LOST

(75) Inventor: Wolfgang Pade, Illingen (DE)

(73) Assignee: Robert Bosch GmbH, Stuttgart (DE)

( * ) Notice: Subject to any disclaimer, the term of this patent is extended or adjusted under 35 U.S.C. 154(b) by 91 days.

(21) Appl. No.: 10/311,498
(22) PCT Filed: Apr. 11, 2002
(86) PCT No.: PCT/DE02/01351
§ 371 (c)(1), (2), (4) Date: Jul. 24, 2003
(87) PCT Pub. No.: WO02/087025
PCT Pub. Date: Oct. 31, 2002

(65) Prior Publication Data
US 2004/0092162 A1 May 13, 2004

(30) Foreign Application Priority Data
Apr. 19, 2001 (DE) .................................. 201 06 745 U

(51) Int. Cl.⁷ .............................................. H01R 13/66
(52) U.S. Cl. ...................................................... 439/620
(58) Field of Search ................................ 439/620, 275, 439/274, 578, 587

(56) References Cited

U.S. PATENT DOCUMENTS

| 5,240,433 A |   | 8/1993 | Kato |
|---|---|---|---|
| 5,356,304 A | * | 10/1994 | Colleran ..................... 439/205 |
| 5,618,198 A | * | 4/1997 | Sato et al. .................. 439/274 |
| 5,756,972 A | * | 5/1998 | Vranicar et al. ............ 219/541 |
| 6,132,256 A |   | 10/2000 | Morsdorf et al. |

FOREIGN PATENT DOCUMENTS

WO    WO 99 63632    12/1999

* cited by examiner

Primary Examiner—Phuong Dinh
(74) Attorney, Agent, or Firm—Kenyon & Kenyon

(57) ABSTRACT

To make possible a very small and compact embodiment of a coupler plug, especially for use for a planar broadband lambda probe having an adjusting unit, the coupler plug being essentially made up of a housing, namely a base element and a cover element as well as seals, which seal off the interior of the housing from the exterior, and having an adjusting unit for a probe, especially a planar broadband lambda probe, which is mounted in the coupler plug or outside the coupler plug via a further contact element, it is provided that the cover element and the seals constitute a single part and therefore along with the cover element constitute one non-detachable unit. In this manner, it is assured that the seals, which enclose the individual wires that emerge from the coupler plug, can be mounted in one single working or assembly step.

5 Claims, 1 Drawing Sheet ent of the description.# COMPACT COUPLER PLUG, PARTICULARLY FOR A PLANAR BROADBAND LAMBDA PROBE, IN WHICH SINGLE-CONDUCTOR SEALS ARE PREVENTED FROM BEING LOST

FIELD OF THE INVENTION

The present invention relates to a coupler plug, in particular for a planar lambda probe (sensor), made up of a housing, namely a base element and a cover element as well as electrical components that can be inserted and fixed in the housing, and an adjusting element for a probe, especially a planar broadband lambda probe, which is mounted in the coupler plug or outside the coupler plug via a further contact element, as well as at least one seal, which seals off from the interior of the housing the individual wires that emerge from the coupler plug.

BACKGROUND INFORMATION

Coupler plugs of the aforementioned type are usually designed for the connection between a cable harness plug and a lambda probe, the connections in the coupler plug being provided for adjustment, signal, and/or heating of the probe. The lambda probe and the lambda control, in connection with three-way catalytic converters, represent today an effective method for cleaning exhaust emissions. The lambda probe, which, for example, can be inserted into an exhaust system, includes a sensor for determining the oxygen content in the exhaust gas.

The residual oxygen content is well-suited for use as a measured quantity, and it regulates the air-fuel ratio, because it indicates precisely whether the air-fuel mixture is being completely combusted.

In this context, the lambda probe supplies a voltage signal, which represents the momentary value of the mixture composition and which follows the mixture changes. The fuel supply to the engine is controlled by a carburation system in accordance with the signal from the lambda probe in such a way that a stochiometric air-fuel ratio $\lambda=1$ is achieved. Heated or unheated probes are used in accordance with the design of the exhaust gas system and the conditions in which they are used. Outside the field of motor vehicles, other applications of the lambda probe include, e.g., regulating gas motors or oil/gas burners.

In particular, broadband lambda probes are designed in modular form and, in combination with planar technology, facilitate the integration of a plurality of functions. They usually have functional layers, which are made up of a porous protective layer, an external electrode, a sensor film, an internal electrode, a reference gas channel film, an insulation layer, a heating element, a heating film, a resistor or adjustment element, and connection contacts.

Because broadband lambda probes are made up of the combination of a nernet concentration cell (=sensor cell) and a pump cell that transports oxygen ions, it can measure very precisely, not only in the stochiometric point at $\lambda=1$, but also in the lean and rich mixture ranges.

Every probe must be individually adjusted. For this purpose, the probe has a built-in resistor ("mini-hybrid"). The adjustment, which is advantageously performed using a laser beam, is made by properly ablating the resistance layer made up of a ceramic substrate, thereby inducing a change in the resistance, so that an adjustment follows.

One specific embodiment provides for the adjustment unit, i.e., the resistor, to be mounted directly at the probe. A further exemplary embodiment provides for the resistor to be accommodated externally, for example, on a cable harness plug that is coupled to the probe.

Heretofore, the adjustment has been carried out by transporting the housing of the coupler plug, in which the resistor is embedded, to the adjustment station without the cover element. After the appropriate laser processing for the adjustment, the cover element was mounted at a further assembly station.

To prevent the ingress of humidity, contamination or the like into the coupler plug, and to assure that the appropriate atmosphere prevails within the coupler plug, the cover element has additional seals. During assembly, the seals themselves are mounted on the cover element or on the base element in a selective fashion and as a function of the corresponding application case. The seals are made of a rubber-like material, which can be compressed or expanded, to assure that the seal completely and sealingly contacts both the individual wires emerging from the housing as well as the housing, or cover element.

In addition, pressure equalizing elements are mounted on the housing of the coupler plug.

One disadvantage of the design of the coupler plug discussed here can be seen, in particular, in that it is necessary to manufacture both seals as well as cover elements in two distinct working processes, the parts having essentially the same function, namely to seal off the interior of the housing from the environment of a cable harness plug.

A further disadvantage of the design lies in the fact that additional working and assembly steps are necessary to install the seals, which seal off the housing interior from its surrounding environment. In this context, it is necessary in the assembly process to pay special attention to the fact that the seal sealingly contacts both the individual wires emerging from the housing as well as the cover element, i.e., the housing itself.

In assembling a cable harness plug of this type, there is also the danger that seals that are important for the functioning of the cable harness plug can be forgotten.

SUMMARY OF THE INVENTION

An object of the present invention is to refine an embodiment of the coupler plug that is provided especially for a planar broadband lambda probe, so as to make it very easy to assemble.

The objective is achieved in that the cover element and the seal constitute a single piece.

One important advantage of the present invention is that the coupler plug it provides is designed to be a single piece, so that a simple assembly of the cover element on the base element is assured without having to additionally preassemble the necessary seals.

The cover element is advantageously made of PBT (polybutylene terephthalt) or a similar mateial, and the seals are injection-molded directly onto the cover element such that the seal 10 is non-detachably connected to the cover element 4 and constitute a single part.

It can alternatively be provided that the seals are mounted on the cover element before it is assembled. A retainer (loss protector) prevents the seal from detaching from the cover element, for example, when the cover element is being stored.

A further advantageous exemplary embodiment of the present invention is provided for in that the cover element is made so as to be transparent. In this way, it is possible to determine whether the seals have the correct shape and position in contacting both the base element as well as the individual wires extending from the base element.

DETAILED DESCRIPTION

Figure 1:
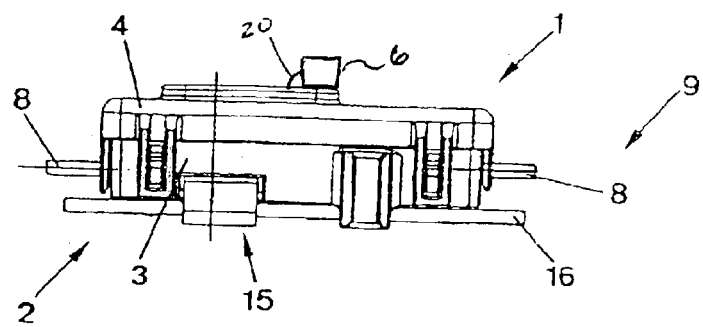
FIG. 1 depicts a side view of the coupler plug according to the present invention, having a closed cover.

Coupler plug 1, depicted in FIGS. 1 through 4, is a type of plug that is made up of a housing 2 that is composed of a base element 2 and a cover element 4. Coupler plug 1 may include electrical components 18 that can be inserted and fixed in the housing 2.

Figure 4:
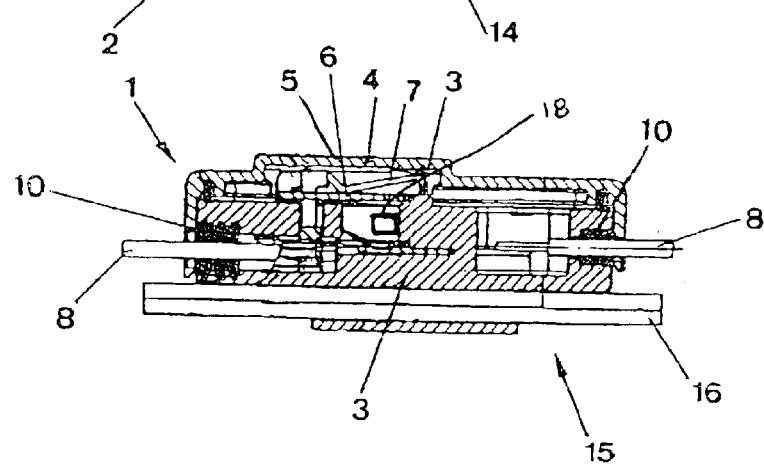
FIG. 4 depicts a cutaway view of the coupler plug according to FIG. 1.

As can be seen in FiG. 4. an adjustment unit 6 is mounted on base element 3 in a holding device 5, the adjustment unit in turn being connected via electrical contact elements 7 to the lambda probe (not depicted in greater detail in the drawings), that is connected via a connecting element in the form of one or a plurality of individual wires 8.

Alternatively, as shown in FIG. 1, the adjustment unit 6 may be accommodated externally and connected via a further contact element 20. Note that only the internal adjustment unit 6, and not the alternative external adjustment unit 6, is shown in the other Figures.

Electrical contact elements 7 are made up of metal strips that are shaped like printed circuit traces, which, in the area of coupling potential 9 of coupler plug 1, terminate in their one side.

Adjustment unit 6 is guided by guide elements (not depicted in greater detail in the drawings), that are configured as part of the holding device 5 and that are mostly mounted on base element 3, and it is held in position by electrical contact elements 7.

Advantageously, coupler plug 1 on its periphery has grooves 14, which permit a coupler plug 1 to be inserted in holders that are provided for this purpose.

Figure 2:
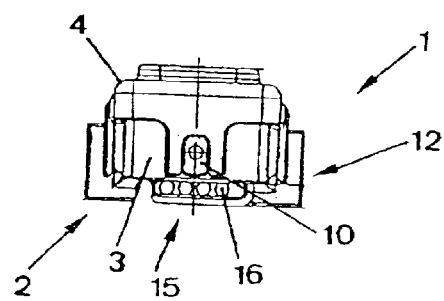
FIG. 2 depicts a rear view of the coupler plug according to FIG. 1.
Figure 3:
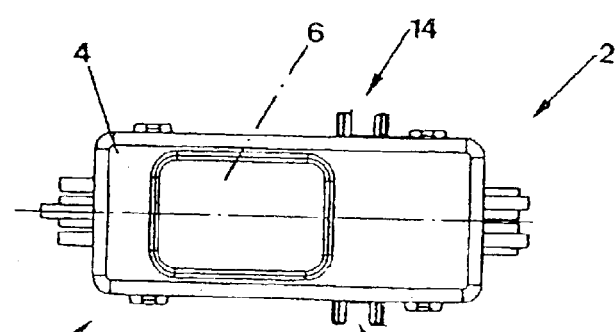
FIG. 3 depicts a top view of the coupler plug according to FIG. 1.

In addition, holding and fixing elements 15 are configured in base element 2, as depicted in FIGS. 1, 2, and 4, the elements making it possible to mount coupler plug 1 on electrical leads 16.

For this purpose, holding and fixing element 15 is configured like a clip, so that coupler plug 1, in the open position of holding element 15, can be plugged into a cable wire (electrical leads 16), and can then be sealed by a further motion.

In this manner, it is possible to secure the coupler plug, for example, on a motor (holder).

In addition, on cover element 4, seals 10 are arranged which, in the mounted state as depicted in the Figures, sealingly contact both cover element 4 as well as housing 2. In addition, individual wires 8 are sealingly enclosed, so that the interior of housing 2 is completely sealed off from the exterior.

Seals 10 are mounted on cover element 4 in a permanent fashion, and during assembly are mounted on base element 3 along with cover element 4.

Due to its small exterior dimensions, it is also possible to accommodate the coupler plug in a grooved tube.

What is claimed is:

1. A coupler plug comprising:
   a housing including a base element and a cover element;
   electrical components adapted to be inserted and fixed in the housing;
   an adjusting element for a probe mounted one of (a) in the coupler plug and (b) outside the coupler plug via a further contact element; and
   at least one seal sealing off, from an interior of the housing, individual wires that emerge from the coupler plug, the cover element and the seat constituting a single part.

2. The coupler plug according to claim 1, wherein the coupler plug is for a planar lambda probe.

3. The coupler plug according to claim 1, wherein the seal is injection-molded onto the cover element.

4. The coupler plug according to claim 1, wherein the seal is adapted to be non-detachably connected to the cover element.

5. The coupler plug according to claim 4, wherein the seal is adapted to be clipped onto the cover element.

* * * * *